United States Patent [19]

Banton et al.

[11] Patent Number: 6,078,051

[45] Date of Patent: Jun. 20, 2000

[54] IMAGE INPUT DEVICE AND METHOD FOR PROVIDING SCANNING ARTIFACT DETECTION

[75] Inventors: Martin E. Banton, Rochester; Stuart A. Schweid, Pittsford; Elizabeth A. Richenderfer, Fairport, all of N.Y.

[73] Assignee: Xerox Corporation, Stamford, Conn.

[21] Appl. No.: 09/004,350

[22] Filed: Jan. 8, 1998

[51] Int. Cl.[7] .................................................. G01N 21/88
[52] U.S. Cl. ........................................ 250/341.1; 358/463
[58] Field of Search ..................................... 250/372, 330, 250/340, 341.1, 568; 382/112; 358/463

[56] References Cited

U.S. PATENT DOCUMENTS 5,017,963  5/1991  Tuhro ........................................ 355/218
5,266,805  11/1993  Edgar ........................................ 250/330

FOREIGN PATENT DOCUMENTS 1547811  6/1979  United Kingdom .
1547812  6/1979  United Kingdom .

*Primary Examiner*—Seungsook Ham
*Assistant Examiner*—Richard Hanig

[57] ABSTRACT

A system and method which enables the location and orientation of an image to be determined without introducing scanning artifacts into the rendered image. The system utilizes a separate set of sensors on a scanning bar that are sensitive to a wavelength of light outside the range of wavelengths of the typical sensors found on the scanning bar, such as red, green, or blue. Moreover, the system includes a light source which is capable of emitting the wavelength of light that is outside this range of wavelength of light. Thus, whenever the additional set of sensors detect light, the system would determine that the light was due to a scanning artifact, such as a hole, rip, or dog ear in the original document being scanned. Furthermore, the system would include a process which measures the variations of the image signal in the fastscan and slowscan directions, as well as, the gray level of the video signal from these various measurements, the system would develop a cost value as to the certainty as whether the signal represents a scanning artifact. In such a system, the backing would be embedded with a pattern which would have a predetermined variation in a fastscan direction but have little or no variation in a slowscan direction.

25 Claims, 11 Drawing Sheets

IMAGE INPUT DEVICE AND METHOD FOR PROVIDING SCANNING ARTIFACT DETECTION

FIELD OF THE PRESENT INVENTION

The present invention is directed to a system which generally scans original documents and converts these documents into electronic image data which can be utilized by a printing system to render the electronic image on a subsequent recording medium. More particularly, the present invention is directed to a system and method for detecting scanning artifacts which are produced during the conversion of the image on a scanned document into electronic image data.

BACKGROUND OF THE PRESENT INVENTION

In the reproduction of copies of an original document from video image data created, for example, by electronic input scanning from an original document, it is often desirable to provide functions dependent upon determining the exterior edges of the document. Such features include, for example, automatic magnification, automatic two-up copying, deletion of background image data which falls outside the detected exterior edges of the document, to avoid storing a document requiring more space than necessary, automatic location of the document in a scanning system, electronic deskewing of the electronic image, etc. In other words, to provide these features, the exterior edges of the document must somehow be detected by the scanning system.

Conventionally, to achieve this detection of the exterior edges of the original document, a background has been provided, for the original document, in the scanning system wherein the background provides a backdrop for the original document, such that the background has a tendency to be distinguishable from the original document. For example, backgrounds have been provided with a yellow color, a black color or a white color with a whiter than white color, a backing which fluoresces, and various other alternatives.

Although various alternatives have been utilized, it is most desirable to utilize a dark backing when scanning an original document so as to eliminate show through when scanning a double-sided or watermarked document. Thus, utilizing a light absorbing backing such as a black color, the scanning system can both eliminate show through when scanning the document and enable the scanning system or other downstream image processing system to automatically locate the exterior edges of the original document so that the various features discussed above can be readily implemented.

However, an undesirable consequence of using a light absorbing backing is that any defects in the original document; such as holes, rips, dog-ears, etc. or other characteristic properties of the original; such as pre-punched holes, etc.; appear as black objects when they are rendered and printed on a recording medium. In the following description, the defects in the original and the characteristic properties of the original will be generally referred to as defects; however, this notation does not imply that the physical properties of the original are actual defects, just properties that create artifacts in the scanning process which are undesirable. This problem can be readily seen from the explanation of FIGS. 1 through 6 of the present application as presented below.

FIG. 1 illustrates a conventional platen scanning system wherein an original document 3 has a defect 5 such as a pre-punched hole. In this platen scanning system, an illumination device 9 provides illumination A which passes through platen glass 7 and defect 5, so that it is reflected off of (or absorbed by) backing 2 of a document cover 1 as reflected light B. This reflected light B is sensed by a photoelectric system 11 comprising electronic sensors which convert the light energy into electronic image data. The photoelectric sensor system ("sensors") 11 may be a charged couple device (CCD), a full width array sensor (FWA), or other photoelectric device which can operate in a black/white mode or a color mode.

As further illustrated in FIG. 1, if the illumination source 9 is moved to position C and the sensors 11 are moved to position D, the light generated from the illumination source 9 is reflected back off the document 3 through the platen glass 7 to the sensors 11, so that the sensors 11 can create electric image data which represents an electronic version of the actual image on the document 3.

In another scanning system, a constant velocity transport system (CVT), as illustrated in FIG. 2, a document 3 having a defect 5 is scanned by the scanning system. More specifically, as illustrated in FIG. 2, a light source 9 generates a light A which passes through a small platen glass 70 and further passes through the defect 5 in the document 3. This light is reflected off the roller or ski 13, which supports the document 3 against or in close proximity to the platen glass 70, as reflected light B which is then received by sensor 11. The CVT system further includes guides 17 and 19 (or alternatively a pair of rollers forming a drive nip therebetween) to guide the original document past the scanning station of platen glass 70 and roller or ski 13. The roller or ski 13 is substantially enclosed in a cavity 15 having a particular backing 20.

As the document is moved past the scanning system, as illustrated in FIG. 3, the defect 5 moves outside of the scanning area such that the light A generated from the light source 9 is incident upon the document 3 and the light reflected back as light B to the sensors 11 represents the actual image on document 3.

In all of the above examples, when the conventional scanning system is scanning the area associated with the defect 5, the sensors 11 are in actuality detecting light reflected from the object immediately behind the document; in the platen, the backing of the platen cover, and in the CVT case, the roller or ski 13. However, when the conventional scanning system is scanning a non-defect area of the document 3, the conventional scanning system is receiving light reflected from the actual image on the document 3. In other words, the electronic image data produced from scanning the entire document 3 would include image data representing the area behind the document as well as the image itself.

For example, as shown in FIG. 4, an original document 3 may consist of an image 4 printed on three-hole pre-punched paper such that the three holes are represented by defect 5. If this document is scanned by the conventional CVT system, as illustrated in FIGS. 2 and 3, wherein the objects and devices behind the document, such as a roller or ski 13, and the cavity 15 are non-reflective, the recorded image 40 on a recording medium 30 would also include dark or black regions 50 (scanning artifacts) which correspond to the defects 5 in the original document 3. On the other hand, as illustrated in FIG. 6, if the document of FIG. 4 is scanned by a conventional platen system, as illustrated in FIG. 1, wherein the backing of the platen cover is white, but is dirty from use, has scratches or otherwise is not of a reflectance equivalent to the document background, it is conceivable that the original image region 4 is reproduced as image region 40 on a recording or display medium 30, and that scanning artifacts may still be present in the form of regions 50 corresponding to the defects 5 of the original document 3. If the platen cover backing was non-reflective, the resulting image would be the same as that illustrated in FIG. 5.

Therefore, it is desirable to be able to scan in an original document having certain defects, as described above, and to ultimately render the image on a recording or display medium void of any evidence of the original defects. In other words, the rendered scanning artifacts 50 of FIGS. 5 and 6 would be eliminated, notwithstanding the fact that the original document 3 included defects 5. Moreover, it is desirable to render or display these images without the scanning artifacts and without sacrificing quality or misidentifying image areas as scanning artifact areas.

SUMMARY OF THE PRESENT INVENTION

Further objects and advantages of the present invention would become apparent from the following descriptions of the various features of the present invention.

In accordance with one aspect of the present invention, there is provided a process for detecting a scanning artifact on a document comprising the steps of: (a) capturing a first set of video image data representing the reflectance of a document, wherein the first set of video image data is generated by sensing light in a visible spectrum reflected from a surface of the document; (b) capturing a second set of video image data representing light in a non-visible spectrum, where the light in the non-visible spectrum is reflected from a surface located adjacent the rear surface of the document and passes through the artifact; and (c) determining, for those regions of the document where the second set of video image data indicates reflected light, that corresponding pixels within the first set of video image data represent an artifact.

In accordance with another aspect of the present invention, there is provided a process for detecting a scanning artifact on a document comprising the steps of: (a) capturing a first set of video image data representing the reflectance of a document, wherein the first set of video image data is generated by sensing light in a visible spectrum reflected from a surface of the document; (b) capturing a second set of video image data representing light in a non-visible spectrum that passes through artifacts in the document, wherein the second set of video image data is generated by sensing light in the non-visible spectrum; and (c) determining, for those regions of the document where the second set of video image data indicates no light was reflected, that corresponding pixels within the first set of video image data represents an artifact.

In accordance with yet another aspect of the present invention, there is provided a digital scanning system for detecting a document artifact, comprising: a visible spectrum light source; a first array of sensors for capturing a first set of video image data representing the reflectance of the document, wherein the first set of video image data is generated by sensing visible spectrum light reflected from a surface of the document; a non-visible spectrum light source; a second array of sensors for capturing a second set of video image data representing light in the non-visible spectrum, where the light in the non-visible spectrum was reflected from a surface located adjacent the rear surface of the document and passed through the artifact; and artifact means for determining, for those regions of the document where the second set of video image data indicates reflected light, that corresponding pixels within the first set of video image data represent an artifact.

In accordance with yet another aspect of the present invention, there is provided a digital scanning system for detecting a document artifact, comprising: a visible spectrum light source; a first array of sensors for capturing a first set of video image data representing the reflectance of the document, wherein the first set of video image data is generated by sensing the visible spectrum light reflected from a front surface of the document; a non-visible spectrum light source positioned to illuminate a surface of the document; a second array of sensors for capturing a second set of video image data representing light in the non-visible spectrum, where the light in the non-visible spectrum passed through the artifact; and artifact means for determining, for those regions of the document where the second set of video image data indicates reflected light, that corresponding pixels within the first set of video image data represent an artifact.

BRIEF DESCRIPTION OF THE DRAWINGS

The following is a brief description of each drawing used to describe the present invention, and thus, are being presented for illustrative purposes only and should not be limiting to the scope of the present invention, wherein.

DETAILED DESCRIPTION OF THE PRESENT INVENTION

Figure 1:
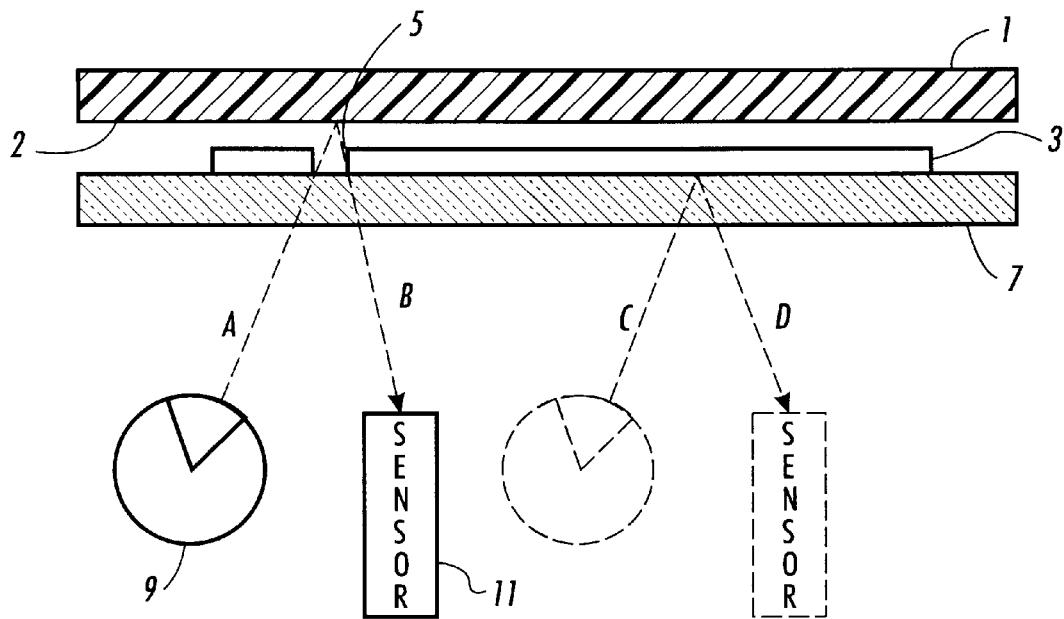
FIG. 1 illustrates an orthographic diagram showing elements of a conventional platen scanning system.

The following will be a detailed description of the drawings illustrated in the present invention. In this description, as well as in the drawings, like reference numbers represent like devices, circuits, or circuits performing equivalent functions.

In the following description, the terms fastscan direction and slowscan direction are utilized. Fastscan direction refers to the scanning of pixels along a scanline or raster. This is also commonly referred to as the electronic scan in that the scanning is a result of collecting image data from an array of photoelectric sensors. Slowscan direction, on the other hand, refers to the direction of the relative movement between the document and the scanning system. This is the mechanical movement that causes the scanning system to generate scanlines of image data.

As noted above, when scanning documents utilizing a digital scanning system, it is desirable to utilize a light absorbing (e.g., black or dark) backing so as to eliminate show through and to enable automatic location and orientation of the original being scanned, thereby enabling auto-registration and electronic deskewing processes to be performed. Furthermore, as noted above, a problem with utilizing a dark backing for copying occurs when documents have defects such as holes, rips, or dog ears.

For example, if a document contains punched holes, the areas corresponding to the punched holes will become black on the copy if a black backing is utilized. This is due to the fact that the captured image has the backing area's gray value (black) wherever the hole is present in the original document. These areas, where the backing area's gray value is present within the original image, are considered scanning artifacts. In most cases, it is undesirable to render the scanning artifact in a copy, especially when the background of the copy is white and the artifact is rendered as black.

To resolve this problem, the present invention proposes a system and method to distinguish if a black or dark area on a document is part of the original image or is an image of the backing of the scanning system resulting from either a hole, rip, dog ear, or other such defect in the original document. In the preferred embodiment of the present invention, the background detected areas can then be replaced with a value which represents the actual background value of the document or a default white value.

To realize this solution, the system must be capable of distinguishing between different object types, more specifically, the actual image of the document and the image data representing the backing behind the document being scanned. To assist in this distinguishing process, the backing of the scanning system should have several properties which are distinguishable from properties normally associated with an image area on a document.

For example, as noted above, it is desirable to have the backing area either a dark color or black. By having the backing area dark, any pixel having a low reflectance value can be considered a potential backing pixel and thus subject to elimination from the rendered image. However, relying solely on the reflectance value of a pixel can produce many false detections so that it is desirable to have a second criteria to measure in order to provide proper distinction between backing and the actual image on the document.

A second criteria which can be utilized to distinguish between backing and an image area is the variation of the gray levels across the backing. It is noted that the variation of gray levels across a typical conventional backing region of an image is very small since the backing tends to be rather uniform in appearance. Also, the variation over the backing region, between successive scanlines, would be very small due to this uniform appearance. However, it is also common to have a uniform area within an image on a document. Therefore, a backing having a typical uniform appearance may not necessarily provide enough information to make a proper distinction between an image area and a backing area.

Figure 7:
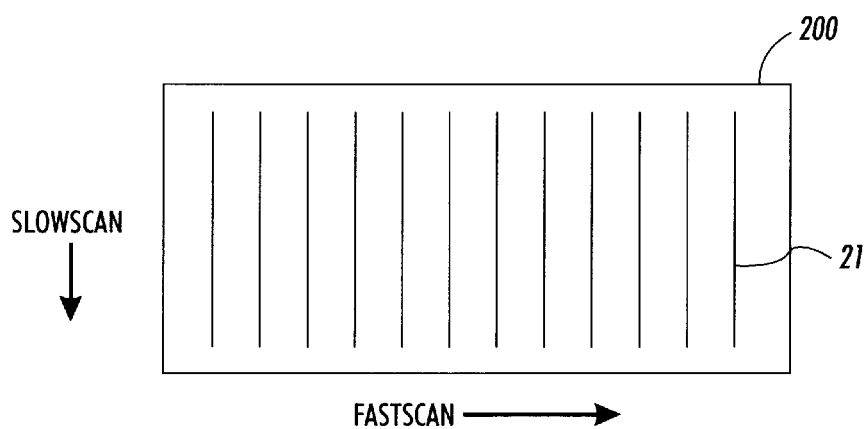
FIG. 7 illustrates an example of a background pattern according to the concepts of the present invention.

To address this situation, the present invention, as illustrated in FIG. 7, provides a backing area which includes an embedded pattern in the backing material. More specifically, as illustrated in FIG. 7, a backing area 200 includes an embedded pattern 21 wherein the embedded pattern periodically repeats itself in a fastscan direction but remains uniform in a slowscan direction. In a preferred embodiment of the present invention, the pattern is embedded in the backing material by cutting slight groves in the backing with a periodic pattern or otherwise creating a surface creating a perceptible pattern in light reflected therefrom. By providing the embedded pattern, the apparent variations of the gray levels along the backing in the fastscan direction increases. Thus, the embedded pattern enables the present invention to generate a signal that has some variation along a given scanline which can be easily detected and recognized as a potential backing pixel. The periodicity of the pattern is selected so as not to correspond to typical halftone frequencies, yet is such that it will be detectable across a relatively small region of the larger image.

Moreover, as illustrated in FIG. 7, the pattern is embedded such that there are little or no variations in the slowscan direction. Providing no or little variation in the slowscan direction can be very helpful in detecting a backing pixel when a constant velocity transport scanning system is utilized, or when trying to discern if the image is a halftone since a halftone will also have some periodicity in the slowscan direction. In a CVT system, the variations in the backing image or pattern from scanline to scanline are small due to the lack of relative motion between the scanbar or scanning system and the backing material because, in a CVT scanning system, the same area of the backing is continually imaged; the variations that are produced are due primarily to electrical noise and undesired relative motion (e.g. vibration).

Figure 10:
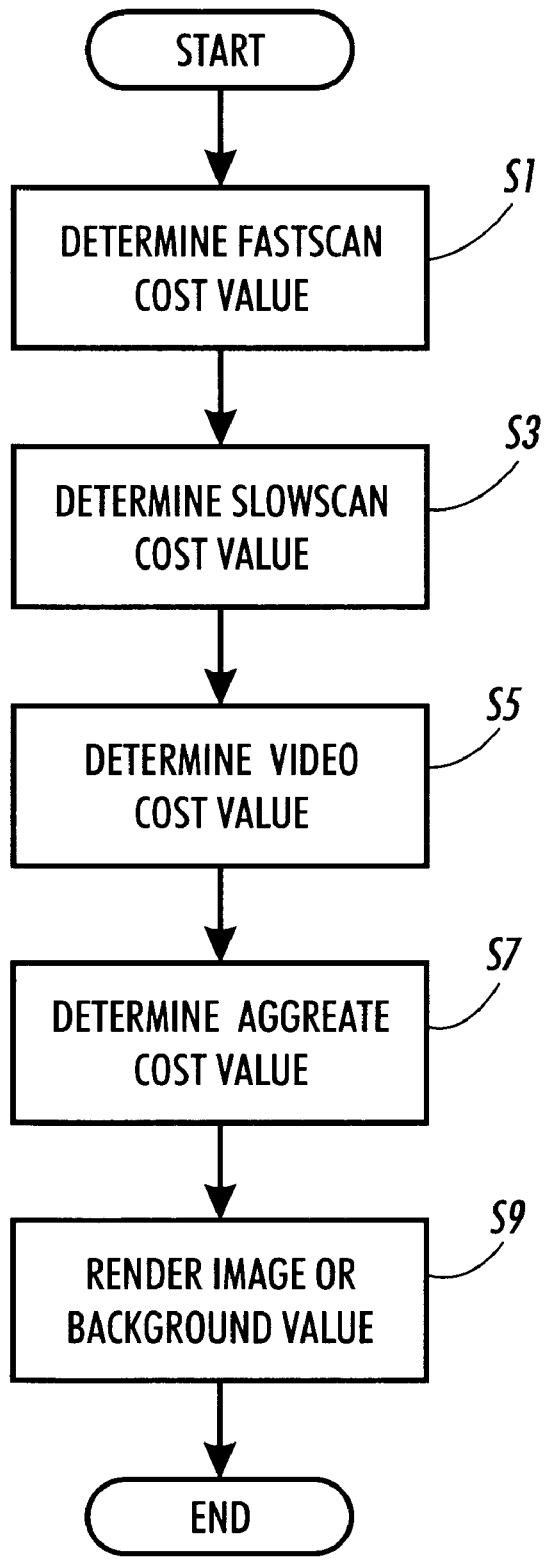
FIG. 10 is a flowchart showing a process to detect a scanning artifact in original document according to the concepts of the present invention.

To utilize these criteria in determining whether a particular pixel within a region is an image pixel (foreground) or a backing pixel, one embodiment of the present invention carries out a process as illustrated in FIG. 10. The process is based upon determining a cost value for a particular decision. For example, the process may determine the cost of classifying the pixel as a halftone versus classifying the pixel as background. In other words, the higher the cost, the less likely the classification will be correct. If the cost is at an acceptable minimum, the classification will be accepted for processing purposes. These cost levels can be adjusted to suit a particular risk comfort level.

The process as illustrated in FIG. 10 determines a fastscan cost value in Step S1. In addition to determining a fastscan cost value, Step S3 determines a slowscan cost value. Furthermore, Step S5 determines a video cost value for the pixel. After these three cost values are determined, an aggregate cost value is calculated at Step S7 wherein this aggregate cost value is utilized in determining whether the pixel is to be classified as a foreground pixel such that the image data is rendered or as a backing pixel wherein a background value is substituted for the image data and this background value is rendered at Step S9.

Figure 11:
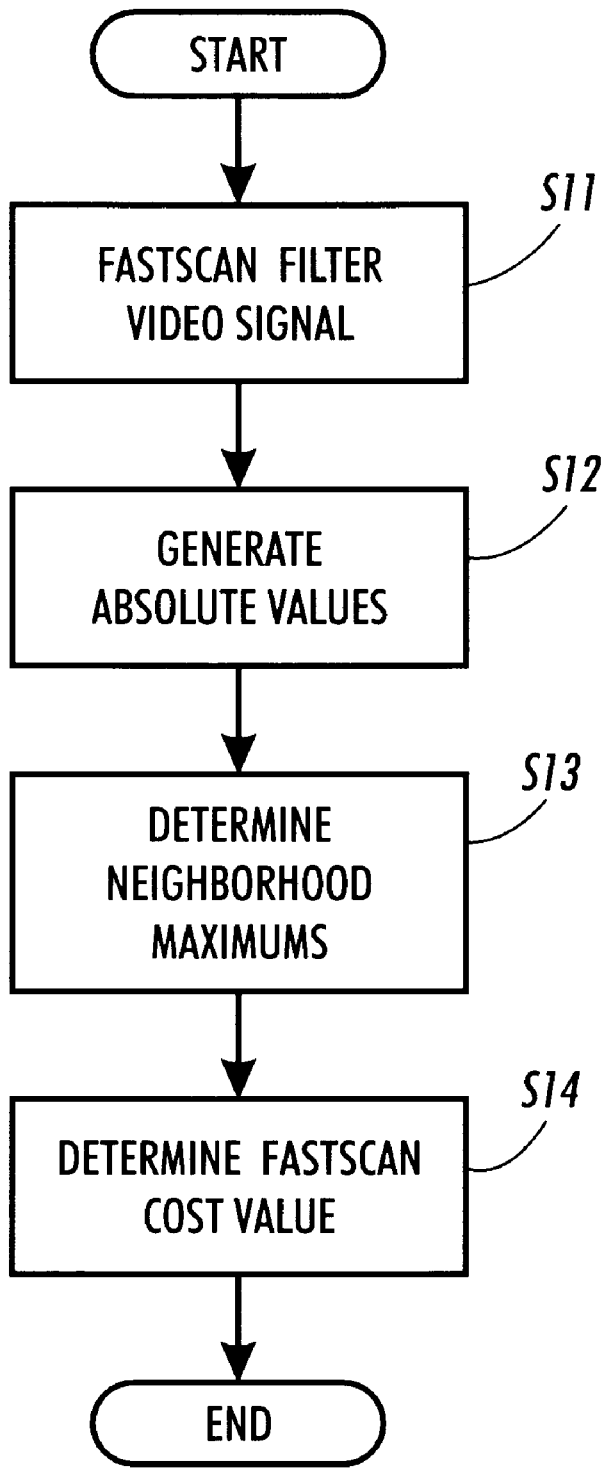
FIG. 11 is a flowchart illustrating a process for determining variations in a fastscan direction according to the concepts of the present invention.

FIG. 11 shows more detail of the process carried out in Step S1 of FIG. 10. More specifically, FIG. 11 illustrates the process for determining the fastscan cost value. In this process, Step S11 fastscan filters the video signal received from the image sensors. The filtered video signal is further processed to generate absolute values for this video signal at Step S12. Utilizing the absolute values of the video signal, Step S13 determines a local maximum value over a predetermined local neighborhood in a fastscan direction. The local maximum values are then utilized to determine the fastscan cost value in Step S14.

Figure 12:
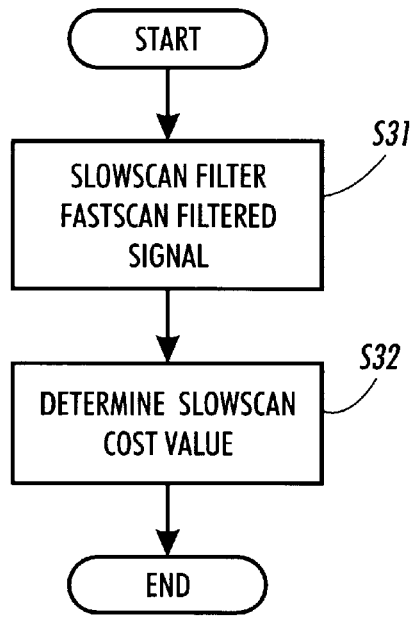
FIG. 12 is a flowchart illustrating a process for determining variations at a slowscan direction according to the concepts of the present invention.

FIG. 12 is a flowchart illustrating, in more detail, the determination of the slowscan cost value as carried out in Step S3 of FIG. 10. More specifically, FIG. 12 illustrates that the process at Step S3 slowscan filters the fastscan filtered video signal which, in the preferred embodiment of the present invention, is generated by Step S11 in FIG. 11. The resulting fastscan/slowscan filtered signal is utilized by Step S32 to determine the slowscan cost value.

Figure 13:
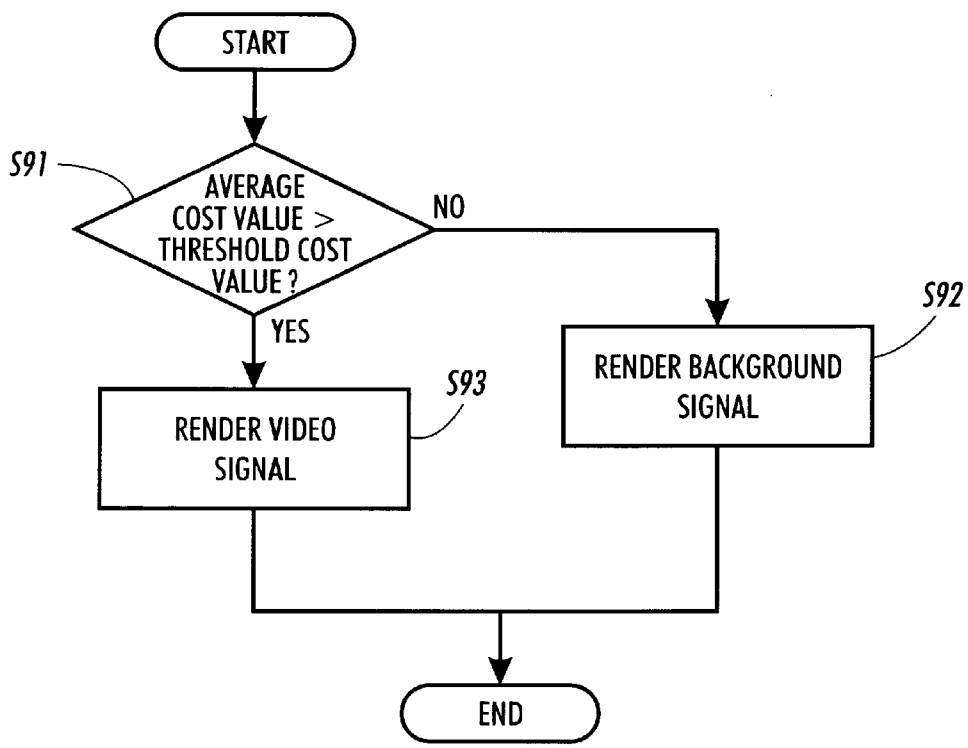
FIG. 13 is a flowchart showing a process to determine and process a scanning artifact according to the concepts of the present invention.

As noted above with respect to FIG. 10, after the three cost values are determined, an aggregate cost value is rendered and this value is utilized to detect the scanning artifact. As illustrated in FIG. 13, Step S91 determines whether an average of the aggregate cost value is greater than a threshold cost value. If the average of the aggregate cost value is greater than the threshold cost value, Step S93 renders the image data associated with the pixel as is, thereby identifying the pixel as representing an image pixel. However, if Step S91 determines that the average of the aggregate cost value is less than the threshold cost value, Step S92 renders a background value for that particular pixel instead of the image data associated with that individual pixel, thereby indicating that the pixel represents a backing pixel. The background value utilized in this rendering process can be either a default value or a calculated background value of the document, as conventionally calculated from a histogram of the document.

It is noted that in the examples discussed above, each criteria has a separate calculated cost value associated with it. In other words, this process for identifying whether a pixel represents a scanning artifact associates a cost to each of the features of the video signals that deviate from the features expected in the background.

For example, if the gray level value of the pixel is a very light gray value, this specific feature will incur a cost since the backing of the scanning system is assumed to be a very dark gray which would produce a dark gray level value for the pixel. On the other hand, if the fastscan variation is very high, the cost will be calculated because the fastscan variations of the pattern in the backing has been established to avoid confusion with a halftone pattern. Lastly, if the slowscan variation is greater that a small threshold, a cost will be assigned because it is assumed that the backing does not vary in the slowscan direction.

Figure 8:
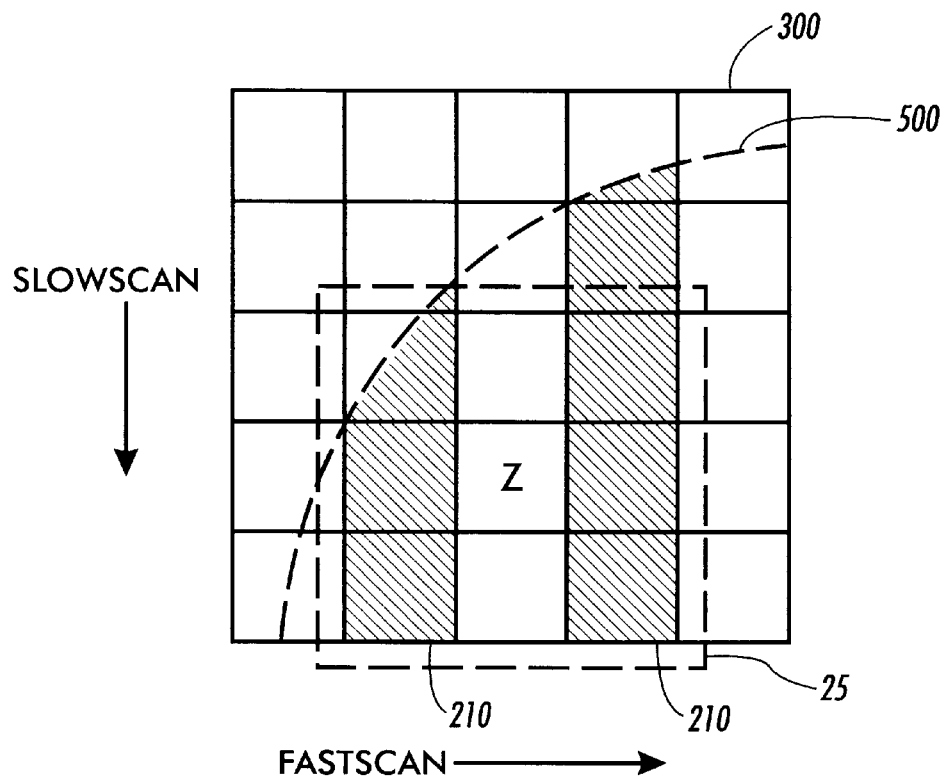
FIG. 8 illustrates a pixel representation of image data generated when scanning a defect area in an original document using the background pattern of FIG. 7.
Figure 9:
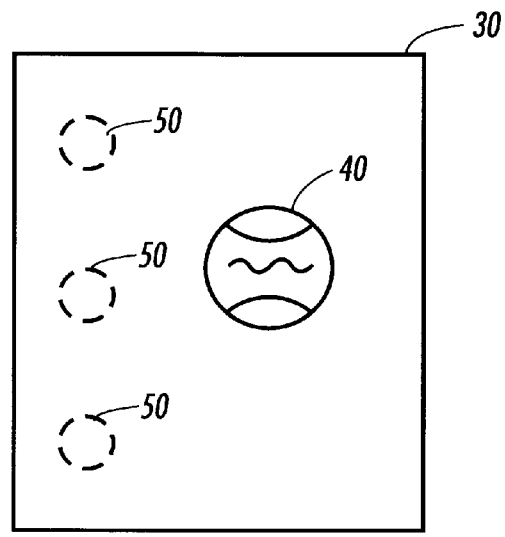
FIG. 9 illustrates a rendering of the original document illustrated in FIG. 4 wherein the defects of the original document are not rendered as scanning artifacts.

The following is a detailed example of the process for identifying a scanning artifact according to a preferred embodiment of the present invention. FIG. 8 will be utilized in describing this example.

In this example, an input scanline of video image data associated with pixel Z of FIG. 8 which lies within a scanning artifact outlined by dotted line 500, initially, is filtered to create a signal F. The filter used to create the signal F is a bandpass filter. It is designed to have peak gain at the embedded pattern frequency of the backing. This will ensure that the pattern 210 of FIG. 8 is amplified. To simultaneously attenuate the high frequency noise (that is inherent in the electronics), the filter has low gain at high frequency. Finally, the filter has a very low gain at very low frequencies to eliminate any of the variation in gray level due to slow varying intensity variations of the lamp. An example of a sufficient bandpass filter is:

$$f=[-0.25\ -0.5\ -0.25\ 0.5\ 1\ 0.5\ -0.25\ -0.5\ -0.25]$$

The filter f is applied in the fastscan direction of the scanned image, V, preferably with a context of at least ten pixels, resulting in F. The image F is further processed by taking the absolute value of each pixel.

$$F_a(i,k)=|F(i,k)|$$

A local maximum signal, M, is then created by subsequently taking the maximum value of F over a local neighborhood in the fastscan direction (in a given scanline k).

$$M(i)=\max(F_a(I)),\ i-n<=|>=i+n$$

The signal M is then used to increment a cost/penalty for the backing match on a pixel by pixel basis. The pixel value of M is compared to pre-calculated upper and lower limits, and if it is out of this range, the cost or penalty added to this pixel is equal to the pixels deviation from the range:

$$\text{if } (M(i)>T_{Mu})C(i)=C(i)+M(i)-T_{Mu}$$

$$\text{else if } (M(i)<T_{Ml})C(i)=C(i)+T_{Ml}-M(i)$$

The lower limit is to give a cost to either electronic originals (that have no fastscan variations) or very smooth originals (such as photographs). These smooth dark areas will not incur any other cost; their line to line variation and black values will be well within range of the backing image statistics. Therefore, the lower limit is what is used to eliminate the photographs from being falsely detected. The upper limit helps remove true line-screen halftones that could be in the image. These halftones have ranges that are much greater than the pattern engraved into the backing, and so the upper limit is a good distinguishing characteristic.

As noted above, slowscan variation is a distinguishing feature. Recall that since the backing image varies slowly over time, variation measurement between successive scanlines can be used. Similar to the fastscan filter characteristics, the slowscan filter chosen is bandpass as well. The low frequencies must be eliminated to remove any illumination (lamp) variations over time. Similarly, the very high frequencies must be eliminated to remove the white noise inherent in the measurement process. One such simple bandpass filter is:

$$g=[1\ 0\ -1]$$

The filter g is applied in the slowscan direction to the fastscan filtered image F of Pixel Z in FIG. 8 across at least three scan lines with Z being in the centered scanline, resulting in G. The image G is further processed by taking the absolute value of each pixel.

$$G_a(i,k)=|G(i,k)|$$

Similar to the fastscan limits, a slowscan upper limit is applied to the output image $G_a$. This is because the background ski or roller is expected to have very slow variations from scanline to scanline. If $G_a$ is above a given threshold, a cost (or penalty) is associated with the given pixel; i.e., if $(G_a(i,k)>T_G)C(i)=C(i)+G_a(I,k)-T_G$ The final component of the cost function is a function of the gray value V(i,k) of the input image pixel Z. The background is known to be near black. If the measured gray value is above the 4 sigma light point of the backing, a cost is associated with that pixel; i.e., if $(V(i,k)>T_v)C(i)=C(i)+V(i,k)-T_v$ where $T_v$ is set to the 4 sigma light point of the backing.

In summary, in this example, pixel Z has a cost associated with it that is the aggregate of three individual costs:

Variation of fastscan filtered data outside a range;

Too large a variation of the slowscan filtered data; and

Too high input video gray level

In the final stage of the detection process, the cost image is averaged using a rectangular blur filter, resulting in $C_{ip}$. This gives the average cost at each pixel in a given neighborhood defined by window 25 such that pixel Z is the center of the window. This cost function is then compared to a threshold to determine if the pixel Z is in the image or from the backing:

if $(C_{ip}(i)>T_c)V_{out}(i)=V_{in}(i)$ else $V_{out}(i)=W$ where $T_c$ is a static threshold value and W is a background value wherein the background value may either be a default value, a user-programmable value, or a calculated background value conventionally generated from a histogram of the original document.

Large deviations between the measured gray statistics and the black backing statistics result in large costs, which are interpreted as the "cost" for converting a pixel to white. The pixel is therefore left alone, and assumed to be part of the image. Pixels with small "cost" values are converted to white, default value, or calculated background value.

Although the process above indicates that three cost values are utilized to detect the scanning artifact, various subcombinations of these cost values can be effectively utilized in various scanning systems. For example, in a platen scanning system, the slowscan cost value may be effectively eliminated since the scanning system is not continually imaging the same backing area; because in such a system the scanning system moves while the document remains stationary. Thus, slowscan variations are to be expected and thus trying to assign a cost value may do more harm than good. In such a system, only the fastscan cost value and video cost value would probably be used.

Figure 18:
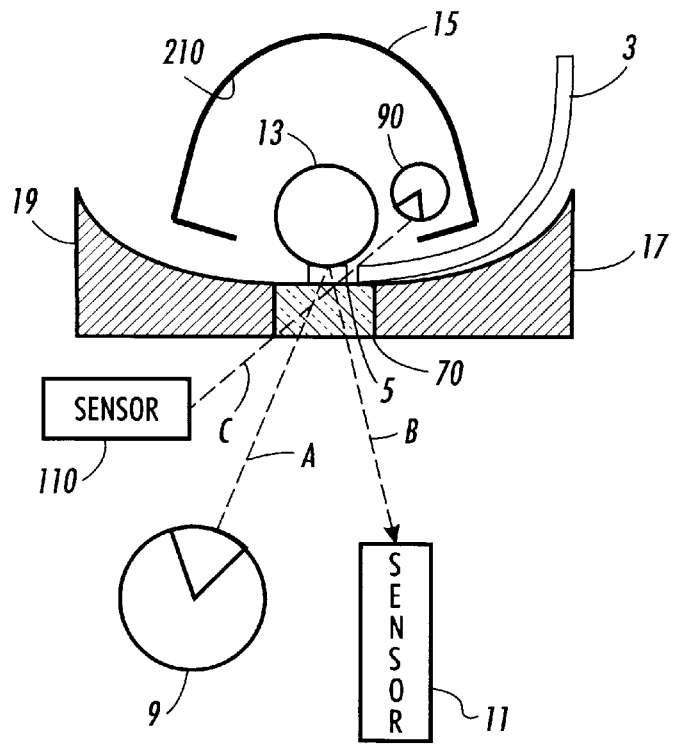
FIG. 18 illustrates a third embodiment of the present invention which utilizes optical properties to determine the presence of a scanning artifact.

In another example, such as a CVT system, as illustrated in FIG. 18, the fastscan cost value would be ineffective because the detected backing image would be a light source which has no pattern. Thus, in this example, only a slowscan cost value and a video cost value would be measured.

Lastly, in a third example, wherein the scanning system utilizes a set of sensors which are designed to be responsive to the image on the document and be saturated when scanning the backing, and another set of sensors which see black when scanning the backing due to the backing reflectance. In other words, a main set of sensors may have a red filter, a second set of sensors with a green or blue filter, and the backing would be colored cyan. In such an example, the red sensor will see the cyan as black and the document as an image. The green sensor would provide the image data (it would be saturated when scanning the backing) to the circuitry detecting the scanning artifact, and since this data is already correlated to the backing due to the color relationship between the backing and the sensor, only fastscan and slowscan cost values need to be calculated.

Figure 14:
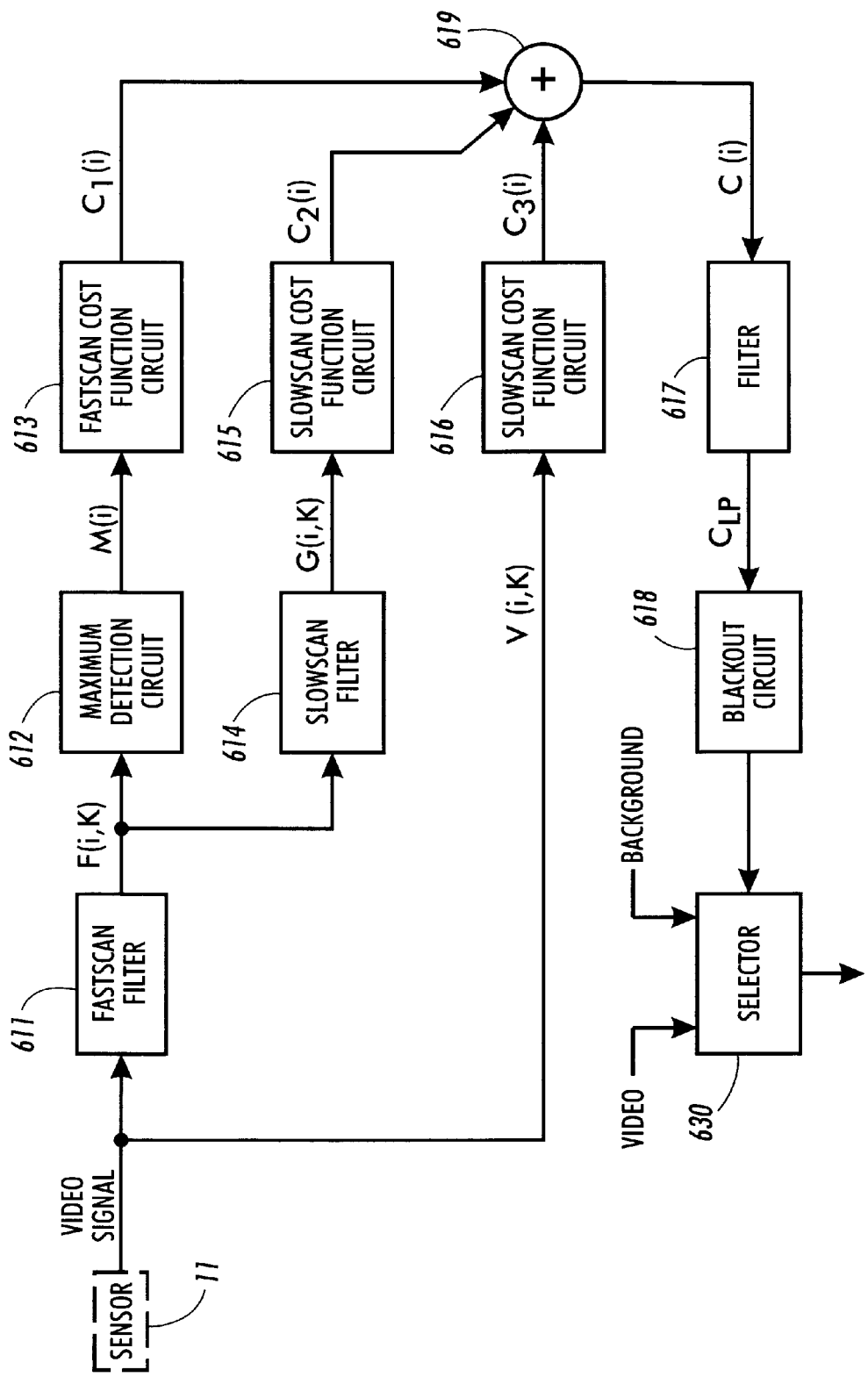
FIG. 14 is a block diagram illustrating a circuit for determining the presence of a scanning artifact according to the concepts of the present invention.

FIG. 14 is a block diagram of a circuit, according to one embodiment of the present invention, which is utilized to detect whether a pixel represents a scanning artifact or not. As illustrated in FIG. 14, a video signal created by the sensors 11 is fed to a fastscan filter 611 which produces a fastscan filtered signal F(i, k). The video signal is also fed to a video cost function circuit 616 which produces a cost value $C_3(i)$.

The fastscan filtered signal, F(i,k) is then fed to a maximum detection circuit 612 and a slowscan filter 614. The maximum detection circuit 612 analyses the filtered signal to produce a local maximum signal M(i) which is fed to a fastscan cost function circuit 613. The fastscan cost function 613 determines the cost value in the fastscan direction and produces a cost value signal $C_1(i)$.

On the other hand, the slowscan filter 614 produces a signal G(i,k) which has been filtered in the fastscan direction and the slowscan direction. This signal G(i,k) is fed to a slowscan cost function circuit 615 which produces a cost value signal $C_2(i)$.

The various cost value signals $C_1(i)$, $C_2(i)$, and $C_3(i)$ are fed to an accumulator 610 which sums the various cost signals together to generate an aggregate cost signal C(i). The aggregated cost value for the pixel is fed through a filter 617, which in the preferred embodiment is a rectangular blur filter applied over a number of neighboring pixels, to produce a signal which is an average of the cost value signal for a particular pixel. This average signal $C_{ip}$ is fed into a background circuit 618 which makes a final determination as whether the pixel represents an image foreground signal or a backing signal. Depending upon this determination, the background circuit feeds a control signal to a selector 630 which either allows the image signal to pass through unprocessed or replaces the image data associated with that pixel with a background value wherein the background value may either be a default value, a user-programmable value, or a calculated background value conventionally generated from a histogram of the original document.

The various thresholds and ranges discussed above and utilized in determining the cost values and the actual classification of the pixel can be either preset in the system as default values or the values can be generated during a calibration process wherein the calibration process would take a scan of the backing without a document to determine the variations of the pattern as well as the different parameters needed to make an actual determination as to whether a pixel represents the backing or the image.

Moreover, a fourth criteria could be added to the process above wherein the geometry (e.g., size) of the scanning artifact is detected, for example, to verify whether the size falls within a predetermined range. If the size of the scanning artifact falls outside that range, it could be determined that the pixel actually represents an image foreground region and not the backing of the scanning system.

In another embodiment of the present invention, the scanning artifact is detected utilizing a process that relies on the wavelength of the light being utilized to detect whether a scanning artifact is present rather than an actual pattern which is embedded in the backing. More specifically, in this embodiment of the present invention, a separate set of sensors is employed. The separate set of sensors being sensitive to a wavelength of light outside visually perceptible wavelengths and/or the visible range sensors which are used in a typical scanning environment such as red, green, or blue. In the preferred embodiment, the wavelength of light used is either in the infrared spectrum or the ultraviolet spectrum.

Moreover, this embodiment also has an additional or modified light source that emits light that can be detected only by the new separate set of sensors and not by the sensors typically used in a document scanning system. This light source would be designed so as not to emit or reflect light that could be detected by the other sensors. Thus, whenever the new set of sensors detect the light, the system would know that the light was due to a defect in the document, and thus the associated pixels, would represent scanning artifacts. These regions of the electronic document would then be treated as background and printed accordingly, thereby eliminating any objectionable scanning artifacts.

Figure 15:
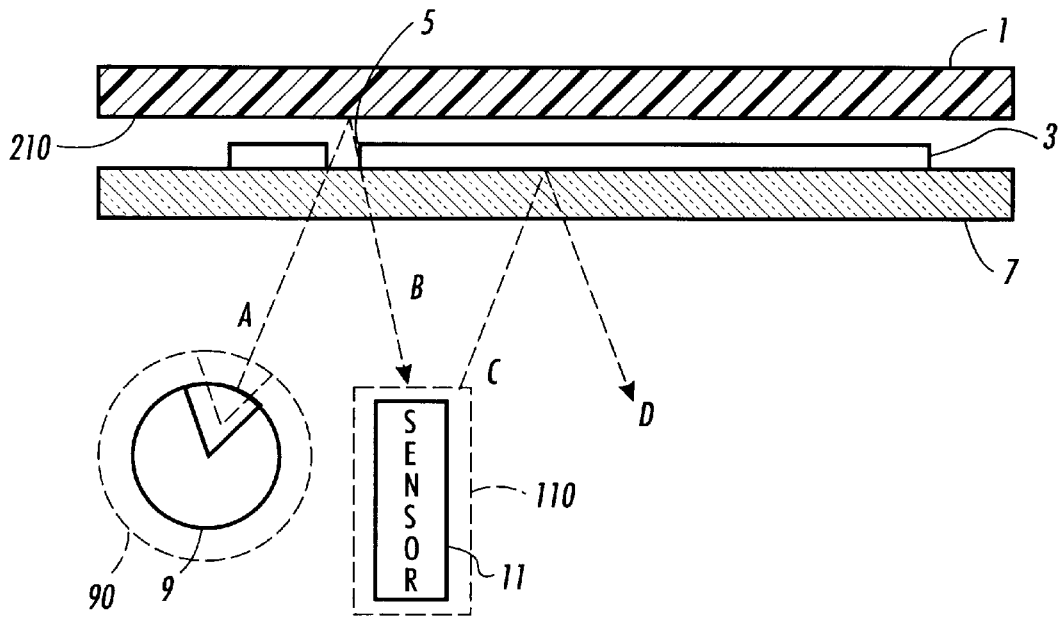
FIG. 15 is a block diagram illustrating another embodiment of the present invention which utilizes optical properties to detect the presence of scanning artifacts.

An example of such an embodiment is illustrated in FIG. 15. FIG. 15 illustrates a platen scanning system very similar to the system illustrated in FIG. 1 with the addition of a second light source 90 and a second set of sensors 110. The sensors 11 and 110 can be manufactured on the same sensor array bar or they may be manufactured such that they are separate sensors. The second light source 90 would emit a light that could only be seen by the new set of sensors 110. The light emitted by the original light source 9 would emit light that can be seen by the original sensors 11, but not by the new set of sensors 110.

In another embodiment utilizing the same concept, the two light sources 9 and 90 would be combined into a single light source which would emit light over the entire spectrum of the sensitivity of the sensors 11 and 110. In this example, wherein a single light source is utilized, the backing material 210 of the document cover 1 would be modified so as to selectively or primarily reflect only the incident light at a wavelength to which the sensors 110 are sensitive. Thus, whenever these sensors 110 are excited, the system would determine that the light came from light being reflected off the backing material and thus classify the associated pixel within such a region as being a backing pixel representing a scanning artifact.

However, in cases where the original document may also reflect the light to the new set of sensors 110, the backing 210 of the document cover 1 would be modified to make sure that the backing always reflected a higher fraction of the light back to the new set of sensors 110 than the document itself reflects back to the sensors 110 so that a thresholding procedure could be used to distinguish when the light detected by the sensors 110 came from the document or the backing. Alternatively, one of the previously characterized methods of imparting a pattern to the reflected light may also be employed to improve the robustness of the scanning artifact recognition operations described above.

Figure 2:
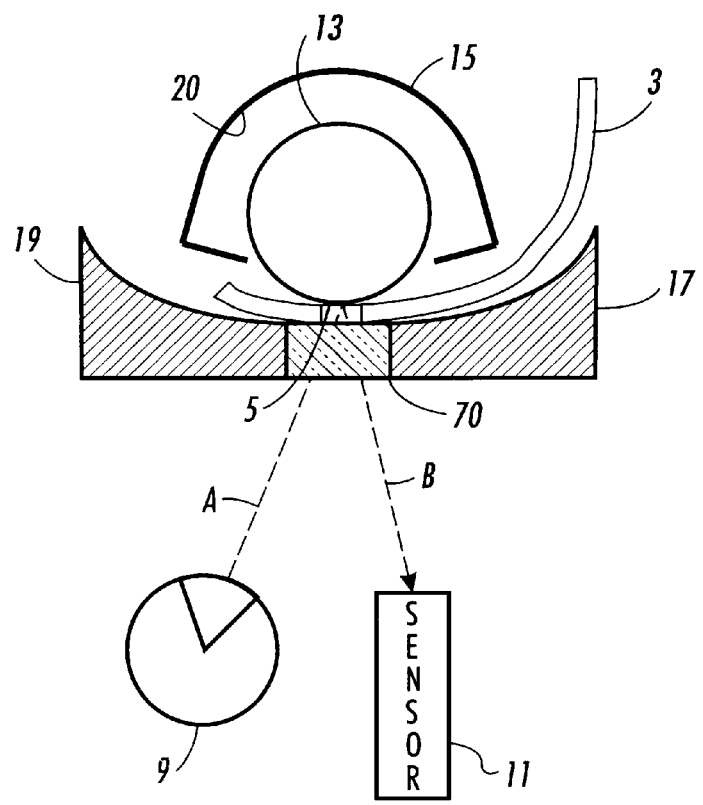
FIGS. 2 and 3 illustrate a conventional constant velocity transport scanning system.
Figure 3:
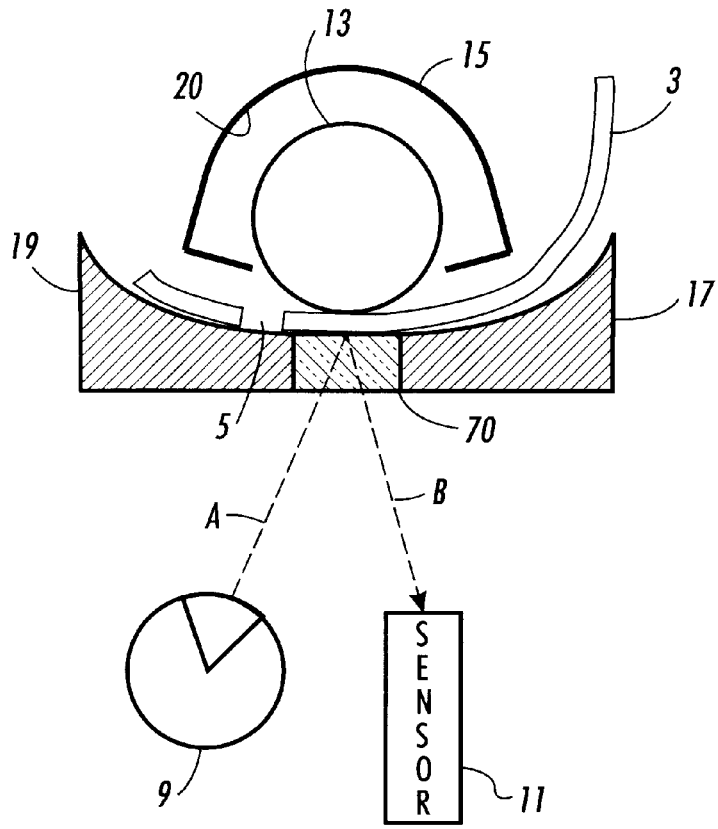
Figure 4:
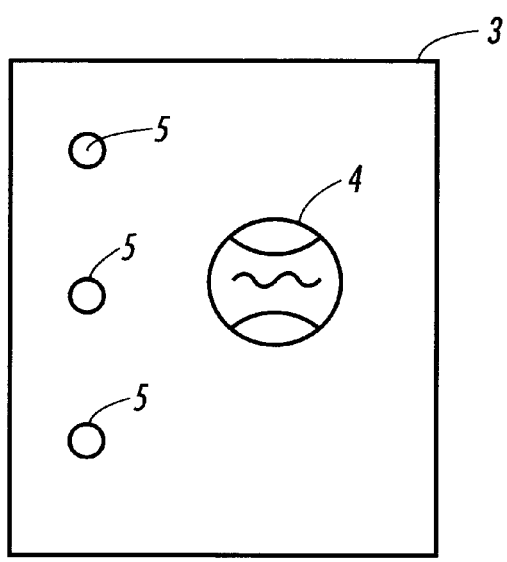
FIG. 4 illustrates an example of an original document with a defect.
Figure 5:
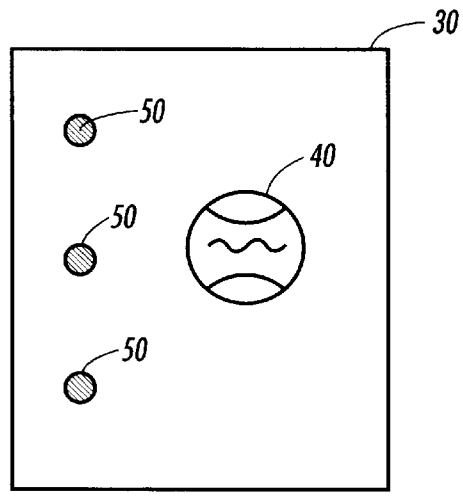
FIGS. 5 and 6 illustrate examples of rendered or displayed copies of the original document illustrated in FIG. 4 utilizing conventional canning/reproduction systems.
Figure 6:
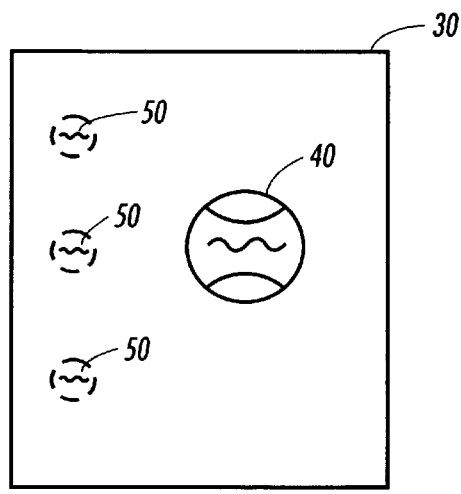
Figure 16:
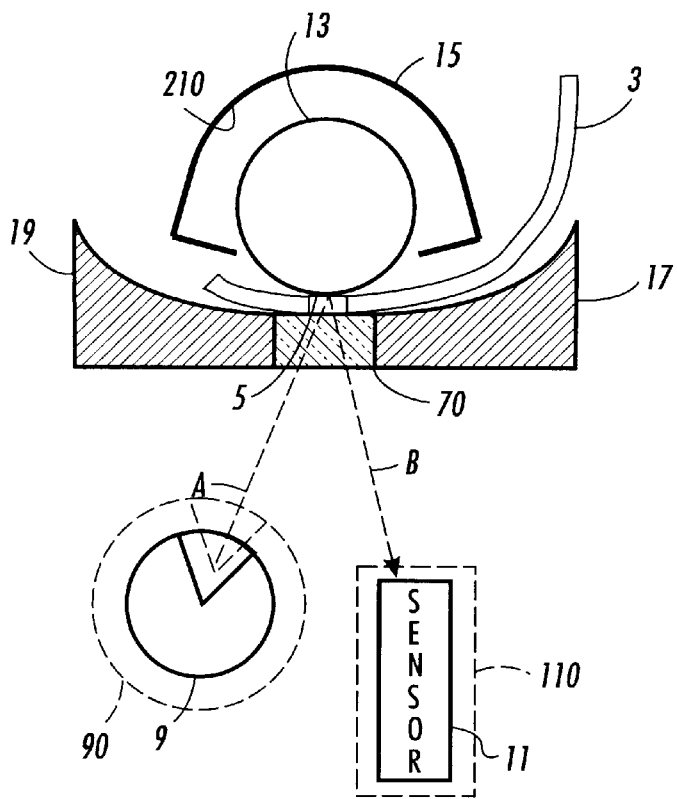
FIGS. 16 and 17 illustrate another embodiment of the present invention which utilizes optical properties to detect the presence of scanning artifacts.
Figure 17:
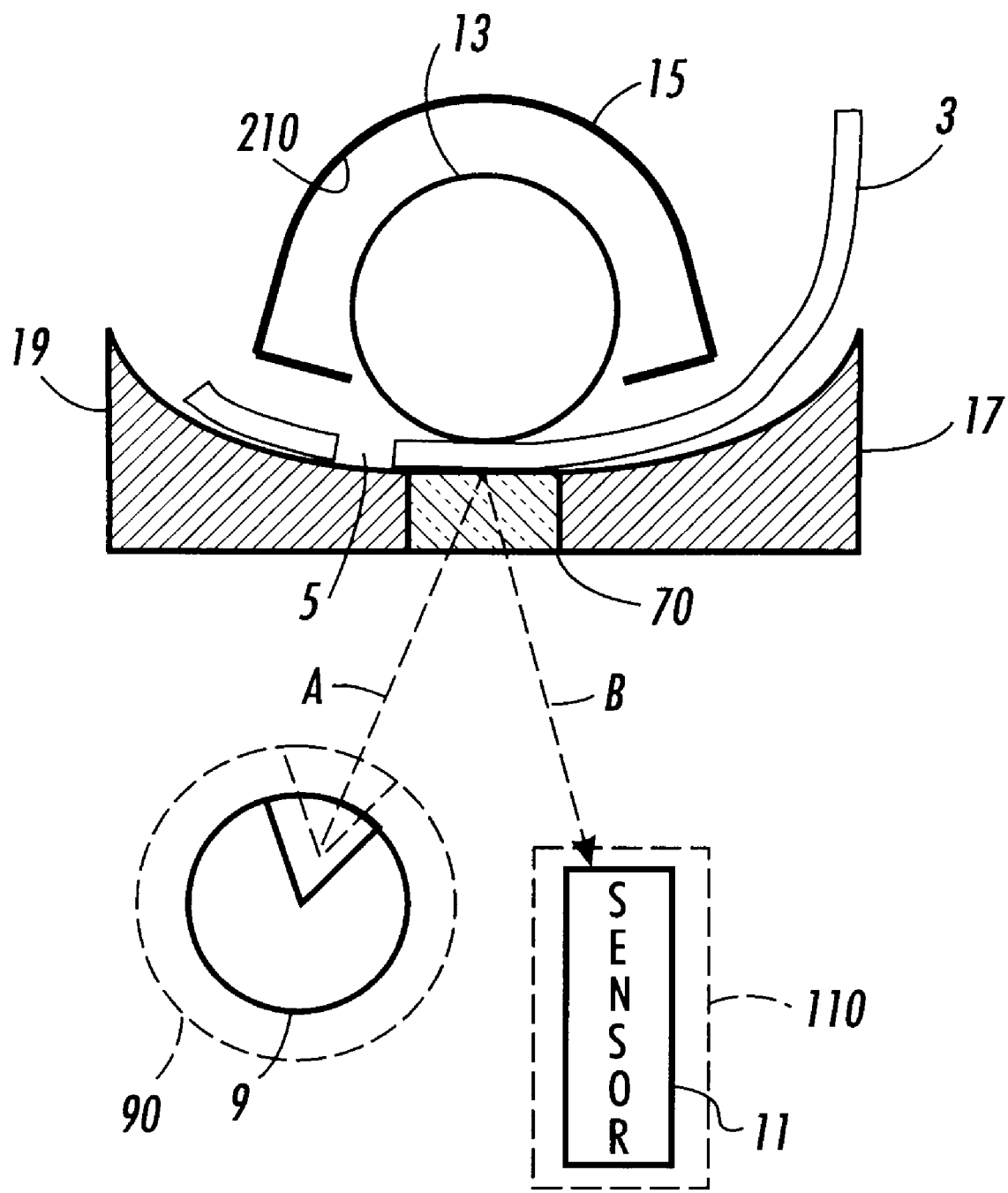

In carrying this concept over to a CVT scanning system, FIGS. 16 and 17 illustrate an embodiment which utilizes the wavelength of light to determine whether a pixel represents a scanning artifact. FIGS. 16 and 17 are essentially the same as FIGS. 2 and 3 except for the addition of the second light source 90 and the second set of sensors 110. As mentioned above, the sensors 11 and 110 can be manufactured on the same sensor array bar or they could be manufactured such that they are separate sensors. The second light source 90 would emit light at a wavelength that could only be detected by the new set of sensors 110. The light emitted by the original light source 9 would emit light that can be detected by the original sensors 11, but not by the new set of sensors 110.

In another embodiment, utilizing a similar concept, the two light sources 9 and 90 would be combined into a single light source which would emit light over the entire spectrum of the sensitivity of the sensors 11 and 110. In this example, wherein a single light source is utilized, the backing material 210 of the cavity 15 or roller 13 would be modified so as to reflect only the light to which the sensors 110 are sensitive. Thus, whenever these sensors 110 are excited, the system would determine that the light came from light being reflected off the backing material and thus classify the associated pixel as being a backing pixel representing a scanning artifact.

However, in cases where the original document may also reflect the light to the new set of sensors 110, the backing 210 of the cavity 15 or roller 13 would be modified to make sure that the backing always reflected a higher fraction of the light back to the new set of sensors 110 than the document reflects back to the sensors 110 so that a thresholding procedure could be used to distinguish when the light detected by the sensors 110 came from the document or the backing.

As an alternative to relying on the light reflecting from the backing to perceive a distinction between the backing material and the document itself, the backing material itself may include an emitter of light of a wavelength that is detectable by the additional set of sensors 110. An example of such a system is illustrated in FIG. 18.

For illustrative purposes only, FIG. 18 shows a CVT scanning system; however, such a system can be readily applicable to a platen scanning system. As illustrated in FIG. 18, an additional light source 90 is positioned on the side of the document 3 opposite that of sensor 110, and may be integrated as part of the backing area of cavity 15 or roll 13. This light source 90 would emit a wavelength or range of wavelengths of light detectable by the additional set of sensors 110. In this example, sensors 110 would detect a defect in the document whenever the light from the light source 90 is able to pass through the document at the defect 5. In other words, if the sensors 110 detects the presence of light emitted from light source 90, the system would be able to determine that those pixels which are associated with the reception of light from light source 90 represent a scanning artifact, a defect in the original document. Thus, the system would be able to process these pixels so as to remove the scanning artifact from the image.

Figure 19:
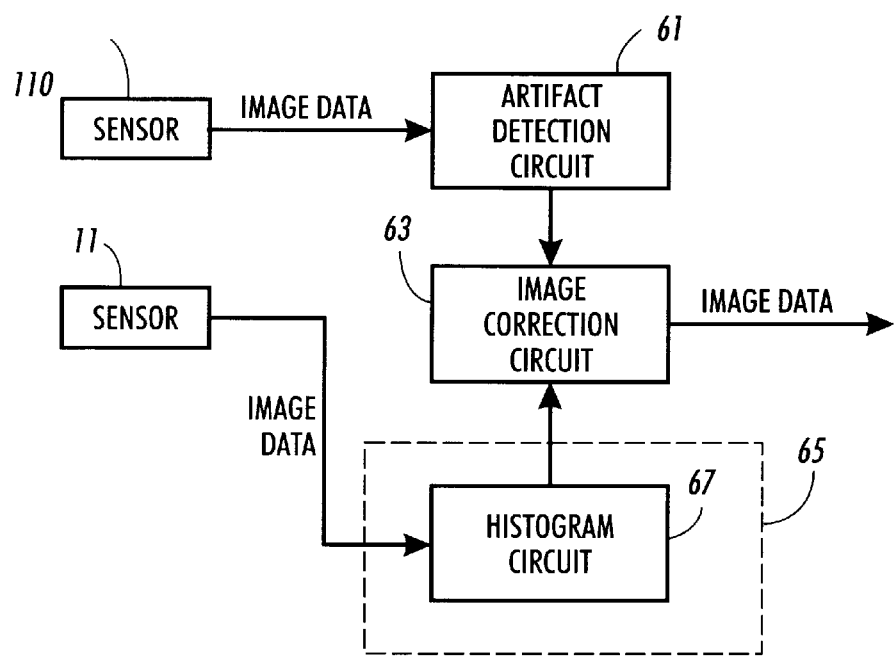
FIG. 19 illustrates a block diagram of a system which detects the canning artifact and corrects the image data therefrom according to the concepts of the present invention.

FIG. 19 illustrates a simple circuit which enables the detection of the scanning artifact and correction of the image data according to this detection. As illustrated in FIG. 19, the image data from the sensor 110 is fed into an artifact detection circuit 61 which detects whether the light from light source 90 has excited the sensors of sensor 110 or not. If the received image data indicates the excitation by the light emitted from light source 90, the artifact detection circuit 61 provides that information to an image correction circuit 63. Image correction circuit 63 also receives the image data from the sensors 11 which represents the actual scanning of the original document 3. If the artifact detection circuit indicates that the pixels represent a scanning artifact, image correction circuit 63 will replace the image data with either a default background value such as white, or an approximated or actual background value of the document being scanned. The actual background value can be generated from an optional background value circuit 65 which would include a histogram circuit 67. Such circuitry is conventional and well known for generating or calculating the actual background value of a document as taught, for example, by Farrell in U.S. Pat. No. 5,282,061, issued Jan. 25, 1994.

It is also noted that the light source 90 would emit light of a wavelength that would not be detectable (or appear as black) to the sensors 11. Moreover, the sensors 110 do not require as high a resolution as do the sensors 11 which do the actual detection of the image on the document. Additionally, the bit resolution (i.e., bits per pixel; generated by the image sensor 110) can be less than the bit resolution of the signals generated by the sensor 11.

With respect to the image correction circuit, whenever it is determined that the sensors 110 have detected light within the boundaries of the original document, those regions of the document would be modified and thereby rendered or displayed with a color appropriate to the background value for that document. This background value could be simply a default value that would always result in marking material being imaged or it could be matched to the detected background of the document itself.

In summary, the present invention provides a system and method for detecting whether a pixel is a result of a scanning artifact and properly processes the image data associated with that pixel accordingly. In one embodiment of the present invention, the present invention utilizes the variation of the video signal in the fastscan and slowscan direction as well as the gray level of the video signal to determine if a pixel represents a scanning artifact. In another embodiment of the present invention, the present invention utilizes the actual wavelength of the light being reflected from the backing or emitted therefrom to determine whether the pixel represents a scanning artifact or not.

The present invention has been described in detail above; however, various modifications can be implemented without departing from the scope of the present invention. For example, the preferred embodiment of the present invention has been described with respect to identifying and correcting an individual pixel which has been identified as a scanning artifact. The present invention can be easily modified such that when a center pixel of a predetermined window of pixels is determined to represent a scanning artifact, all the pixels within that window are then classified as being representative of a scanning artifact. In this embodiment, by classifying all the pixels within the window, the actual area identified as a scanning artifact will be slightly greater than the scanning artifact thereby ensuring proper and entire elimination of the scanning artifact if that is so desired.

Moreover, it is noted that the same process is utilized above to detect the presence of the backing in the video signal, can be used to determine the location and orientation of the original being scanned. More specifically, this process can be utilized to detect the edges of the document; i.e., the transition between the backing and the document itself so as to determine the location the document and the orientation of the document being scanned. This detection would be utilized to develop the parameters of the outer edges of the document so that when the backing area is detected within these outer edges, the backing area can be properly processed, such as elimination of this backing area with the replacement of the image data with a background value.

Lastly, the scanning artifact detection system and method of the present invention can be readily implemented on an application specific integrated circuit, various logic circuits, or in software, thereby enabling the incorporation of this process in a scanner, electronic subsystem, printer, or other image processing device.

While the present invention has been described with reference to various embodiments disclosed herein, it is not to be confined to the details set forth above, but it is intended to cover such modifications or changes as made within the scope of the attached claims.

What is claimed is:

1. A method for detecting a scanning artifact on a document comprising the steps of:
   (a) capturing a first set of video image data representing the reflectance of a document, wherein the first set of video image data is generated by sensing light in a visible spectrum reflected from a surface of the document;
   (b) capturing a second set of video image data representing light in a non-visible spectrum, where the light in the non-visible spectrum is reflected from a surface located adjacent the rear surface of the document and passes through the artifact; and
   (c) determining, for those regions of the document where the second set of video image data indicates reflected light, that corresponding pixels within the first set of video image data represent an artifact.

2. The method of claim 1, wherein the light in the non-visible spectrum is infrared light.

3. The method of claim 1, wherein the light in the non-visible spectrum is ultraviolet light.

4. The method of claim 1, wherein the step of capturing a second set of video image data representing light in a non-visible spectrum, comprises the steps of:
   emitting light from a source capable of producing light in the non-visible spectrum, said source being positioned adjacent a front surface of the document so as to cause light emitted therefrom to be directed toward the front surface; and
   receiving, with a photoelectric sensor system positioned adjacent the front surface of the document, light reflected from at least the surface adjacent the rear surface of the document.

5. The method of claim 4, wherein the source is a wide spectrum light source capable of providing light at both visible and non-visible wavelengths.

6. The method of claim 1, further comprising the step of replacing corresponding pixels within the first set of video image data with a background value when the second set of video image data indicates a scanning artifact.

7. A method for detecting a scanning artifact on a document comprising the steps of:
   (a) capturing a first set of video image data representing the reflectance of a document, wherein the first set of video image data is generated by sensing light in a visible spectrum reflected from a surface of the document;
   (b) capturing a second set of video image data representing light in a non-visible spectrum that passes through artifacts in the document, wherein the second set of video image data is generated by sensing light in the non-visible spectrum; and
   (c) determining, for those regions of the document where the second set of video image data indicates a presence of light, that corresponding pixels within the first set of video image data represents an artifact.

8. The method of claim 7, wherein the light in the non-visible spectrum is selected from the group comprising:
   infrared light; and
   ultraviolet light.

9. The method of claim 7, wherein the step of capturing a second set of video image data representing light in a non-visible spectrum, comprises the steps of:
   emitting light from a source capable of producing light in the non-visible spectrum, said source being positioned adjacent a front surface of the document so as to cause light emitted therefrom to be directed toward the front surface; and receiving, with a photoelectric sensor system positioned adjacent the front surface of the document, light reflected from at least the surface adjacent the rear surface of the document.

10. The method of claim 9, wherein the source is a wide spectrum light source capable of providing light at both visible and non-visible wavelengths.

11. The method of claim 7, further comprising the step of replacing corresponding pixels within the first set of video image data with a background value when the second set of video image data indicates a scanning artifact.

12. A digital scanning system for detecting a document artifact, comprising:

a visible spectrum light source;

a first array of sensors for capturing a first set of video image data representing the reflectance of the document, wherein the first set of video image data is generated by sensing visible spectrum light reflected from a surface of the document;

a non-visible spectrum light source;

a second array of sensors for capturing a second set of video image data representing light in the non-visible spectrum, where the light in the non-visible spectrum was reflected from a surface located adjacent the rear surface of the document and passed through the artifact; and artifact means for determining, for those regions of the document where the second set of video image data indicates reflected light, that corresponding pixels within the first set of video image data represent an artifact.

13. The system of claim 12, wherein the light in the non-visible spectrum is infrared light.

14. The method of claim 12, wherein the light in the non-visible spectrum is ultraviolet light.

15. The system of claim 12, wherein said non-visible spectrum light source is positioned adjacent a front surface of the document so as to cause light emitted therefrom to be directed toward the front surface; and said second array of sensors is positioned adjacent the front surface of the document to receive light reflected from at least the surface adjacent the rear surface of the document.

16. The system of claim 15, wherein the visible spectrum and non-visible spectrum lights sources comprise a wide spectrum light source capable of providing light at both visible and non-visible wavelengths.

17. The system of claim 12, further comprising image processing means for replacing corresponding pixels within the first set of video image data with a background value when the second set of video image data indicates a scanning artifact.

18. The system of claim 17, further comprising printing means for rendering the background values and image data received from said image processing means.

19. A digital scanning system for detecting a document artifact, comprising:

a visible spectrum light source;

a first array of sensors for capturing a first set of video image data representing the reflectance of the document, wherein the first set of video image data is generated by sensing the visible spectrum light reflected from a front surface of the document;

a non-visible spectrum light source positioned to illuminate a surface of the document;

a second array of sensors for capturing a second set of video image data representing light in the non-visible spectrum, where the light in the non-visible spectrum passed through the artifact; and artifact means for determining, for those regions of the document where the second set of video image data indicates a presence of light, that corresponding pixels within the first set of video image data represent an artifact.

20. The system of claim 19, wherein the light in the non-visible spectrum is infrared light.

21. The system of claim 19, wherein the light in the non-visible spectrum is ultraviolet light.

22. The system of claim 19, wherein said non-visible spectrum light source is positioned adjacent a first surface of the document so as to cause light emitted therefrom to be directed toward the first surface; and said second array of sensors is positioned adjacent an opposite surface of the document to receive light passing through the artifacts in the document.

23. The system of claim 22, wherein the visible spectrum and non-visible spectrum lights sources comprise a wide spectrum light source capable of providing light at both visible and non-visible wavelengths.

24. The system of claim 19, further comprising image processing means for replacing corresponding pixels within the first set of video image data with a background value when the second set of video image data indicates a scanning artifact.

25. The system of claim 24, further comprising printing means for rendering the background values and image data received from said image processing means.

* * * * *